United States Patent
Rosenblum et al.

[11] Patent Number: 6,089,079
[45] Date of Patent: Jul. 18, 2000

[54] MOISTURE SENSOR FOR ORE CONCENTRATES AND OTHER PERTICULATE MATERIALS

[75] Inventors: Ephraim Rosenblum, St-Laurent; John M. Lucas, Outremont, both of Canada

[73] Assignee: Noranda Inc., Canada

[21] Appl. No.: 08/862,928

[22] Filed: May 27, 1997

[51] Int. Cl.[7] .......................... G01N 11/00; G01N 11/02; G01N 11/10
[52] U.S. Cl. ................ 73/73; 73/866; 73/54.23; 34/314; 324/321
[58] Field of Search ............... 73/73, 54.23, 866

[56] References Cited

U.S. PATENT DOCUMENTS

| | | | |
|---|---|---|---|
| 3,141,129 | 7/1964 | Dietert | 324/65 |
| 3,355,665 | 11/1967 | Fegan Jr. | 324/65 |
| 3,370,360 | 2/1968 | Smith | 34/48 |
| 3,376,877 | 4/1968 | Fegan, Jr. | 134/57 |
| 3,512,395 | 5/1970 | Valentik | 73/54 |
| 3,724,821 | 4/1973 | Szatmari | 259/149 |
| 3,800,141 | 3/1974 | Beaumer et al. | 250/391 |
| 3,875,504 | 4/1975 | Bodycomb, Jr. et al. | 324/65 R |
| 4,558,393 | 12/1985 | Tanaka et al. | 361/286 |
| 4,780,665 | 10/1988 | Mitchell | 324/65 |
| 5,144,755 | 9/1992 | Braun et al. | 34/52 |
| 5,544,426 | 8/1996 | Yoshida et al. | 34/314 |
| 5,545,371 | 8/1996 | Ly | 264/555 |
| 5,590,976 | 1/1997 | Kilheffer et al. | 404/72 |
| 5,594,340 | 1/1997 | Coyle et al. | 324/321 |

FOREIGN PATENT DOCUMENTS 1077231  7/1967  United Kingdom.

OTHER PUBLICATIONS

Carr–Brion in Moisture sensors in process control, Chapter 5, 46–66.

*Primary Examiner*—Hezron Williams
*Assistant Examiner*—Dennis Loo
*Attorney, Agent, or Firm*—Fitzpatrick, Cella, Harper & Scinto

[57] ABSTRACT

The present invention is concerned with a moisture sensor for measuring the moisture content of particulate material like ore concentrates. The sensor comprises a body having one end to be buried within the bulk of the particulate material and the other end coupled to a force transducer. The force transducer itself is coupled to display means, so that when a conveyor containing the ore concentrate is in operation, a signal is generated from the force transducer and displayed as a result of the drag force exerted by the particulate material on the body. The moisture content may therefore be determined either by means of a calibration chart, or by the output of a calibration computer.

9 Claims, 3 Drawing Sheets

MOISTURE SENSOR FOR ORE CONCENTRATES AND OTHER PERTICULATE MATERIALS

FIELD OF THE INVENTION

The present invention is concerned with a moisture sensor for particulate materials such as ore concentrates. The present sensor is particularly useful for on-line monitoring the moisture content of conveyor borne materials.

BACKGROUND OF THE INVENTION

In the mining industry, the ore concentrate produced at the mine must generally be transported or shipped to other premises for final refining by either electrolysis, smelting etc. The costs associated with transporting and handling these concentrates are not negligible, and attempts have been made to reduce them to the minimum. One specific issue is the control of the moisture content. Such control is critical because it has direct consequences on handling and transportation of the concentrates. Concentrates too dry generate undesirable dust, while excessive moisture content causes the concentrates to stick to the container surfaces, and significantly increases shipping costs because of greater weight. In the mining industry, a generally accepted moisture content for ore concentrates is about 7–9%. Drying of ore concentrates is sometimes carried out in an uncontrolled manner, resulting in a moisture content varying from 5 to 12%. Overdrying concentrates significantly increases energy costs.

Several physical principles and properties have been applied to measure moisture content of various particulate materials. For example, measurements based on electrical conductivity, dielectric properties, microwave absorption etc. are known. They are all affected by the electrical properties of both the concentrate and water, and therefore cannot be employed reliably for conductive concentrates such as copper and lead concentrates. Errors in conductivity-based measurement depend on both dissolved impurities in the water and variations in the nominal concentrate composition.

Sensors using infra-red based measurements have also been developed, but they are affected by the concentrate's optical absorption at wavelengths used to characterize the water content. Further, since measurements take place at the sample's surface, surface drying may prevent measurements from accurately representing the bulk. Finally, water vapor between the sample and the sensor may also adversely influence accuracy.

The sensor disclosed in U.S. Pat. No. 3,800,141 takes measurements based on the selective deceleration of fast neutrons in conjunction with absorption of gamma radiation to establish density. Such measurement technique is complex, potentially hazardous due to the use of nuclear sources, and, as for all the sensors described above, tends to be sensitive to sample presentation.

An excellent review of moisture sensors is provided in Chapter 5 of *Moisture sensors in process control*, authored by K. Carr-Brion (Elsevier Applied Science Publishers). It is mentioned therein that mechanical properties of powders can be used to determine the moisture content therein. For example, the determination of the moisture content in sand is exemplified by correlating the water content with the capacity of sand to pass across slots of different widths. Although methods and sensors using mechanical properties are simple, reliable and relatively cheap, they are, as pointed out by Carr-Brion, highly specific, and require complicated engineering for coupling with computerized control units.

It would therefore be highly desirable to develop a sensor not affected by the electrical and/or optical properties of either the particulate material, or associated moisture. Such sensor would preferably use mechanical properties or drag forces and would be used in a continuous manner. Because the correlation between dust and sticking properties and moisture is incidental, such novel sensor would be particularly useful where moisture control is intended to improve material handling with respect to dust and sticking. Finally, to avoid any misreading or misinterpretation, the sensor should be placed or buried within the particulate material, so that the measurements are representative of the moisture content of the bulk of the particulate material.

SUMMARY OF THE INVENTION

In accordance with the present invention, there is now provided a moisture sensor for on-line measuring the moisture content of moving particulate material such as ore concentrates. More specifically, the present moisture sensor comprises a body coupled to a force transducer; processing means coupled to the force transducer to process signal output from the force transducer, and display means coupled to the processing means to display the moisture content of the particulate material, whereby, the body is buried within the bulk of the particulate material and the signal output is generated from the force transducer as a result of the drag force exerted by the moving particulate material on the body.

In a preferred embodiment of the present invention, the body is a rod having one end buried within the bulk of the particulate material and the other end coupled to the force transducer outside the particulate material, and the end of the rod buried within the bulk of the particulate material is provided with a disk-shape element having its upper and lower surfaces perpendicular to the rod.

In a most preferred embodiment, a signal averager is provided between the force transducer and the display means to average the signal and reduce signal irregularities.

IN THE DRAWINGS

DETAILED DESCRIPTION OF THE INVENTION

Figure 1:
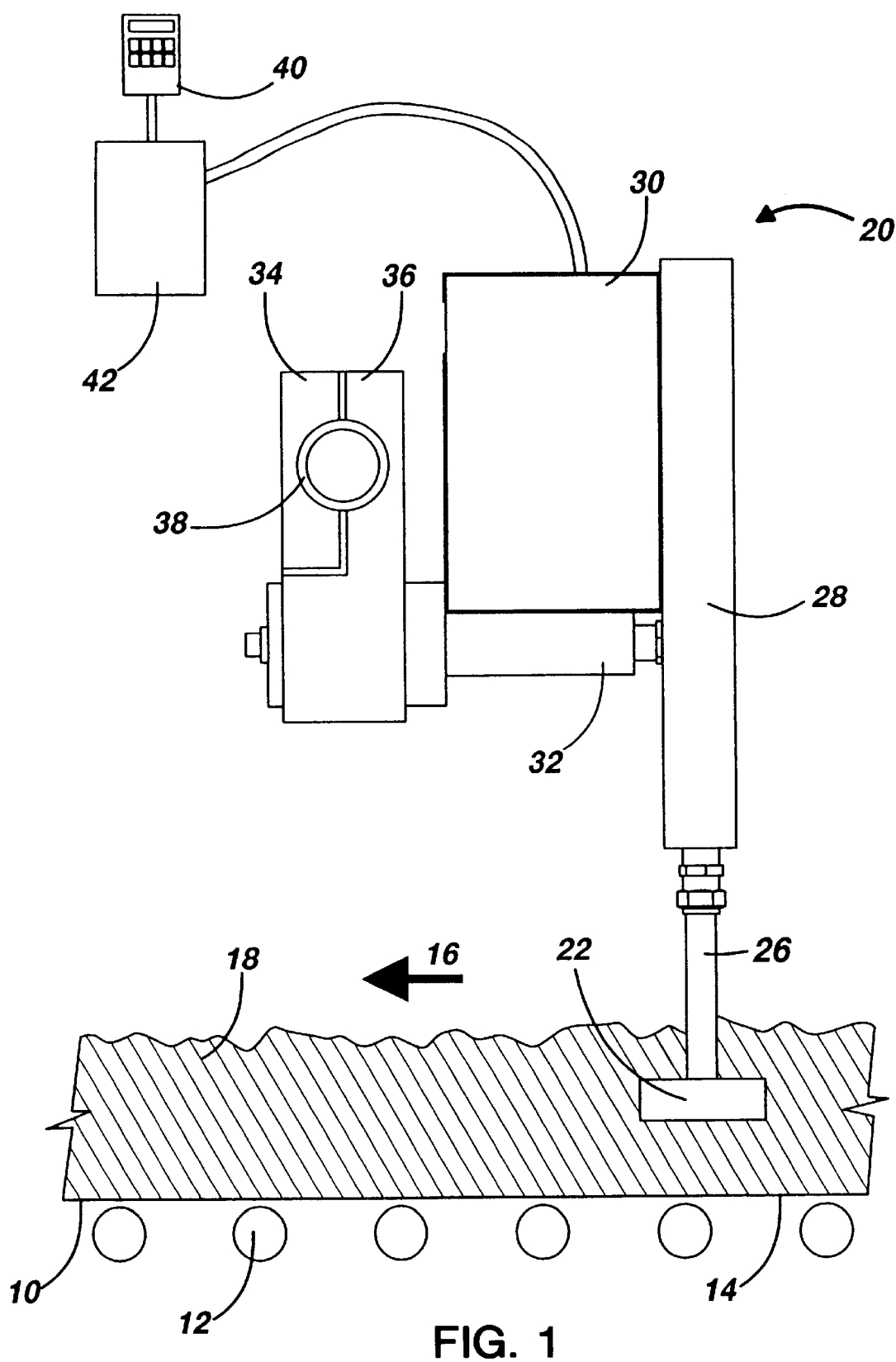
FIG. 1 illustrates a side view of the moisture sensor according to the present invention.
Figure 2:
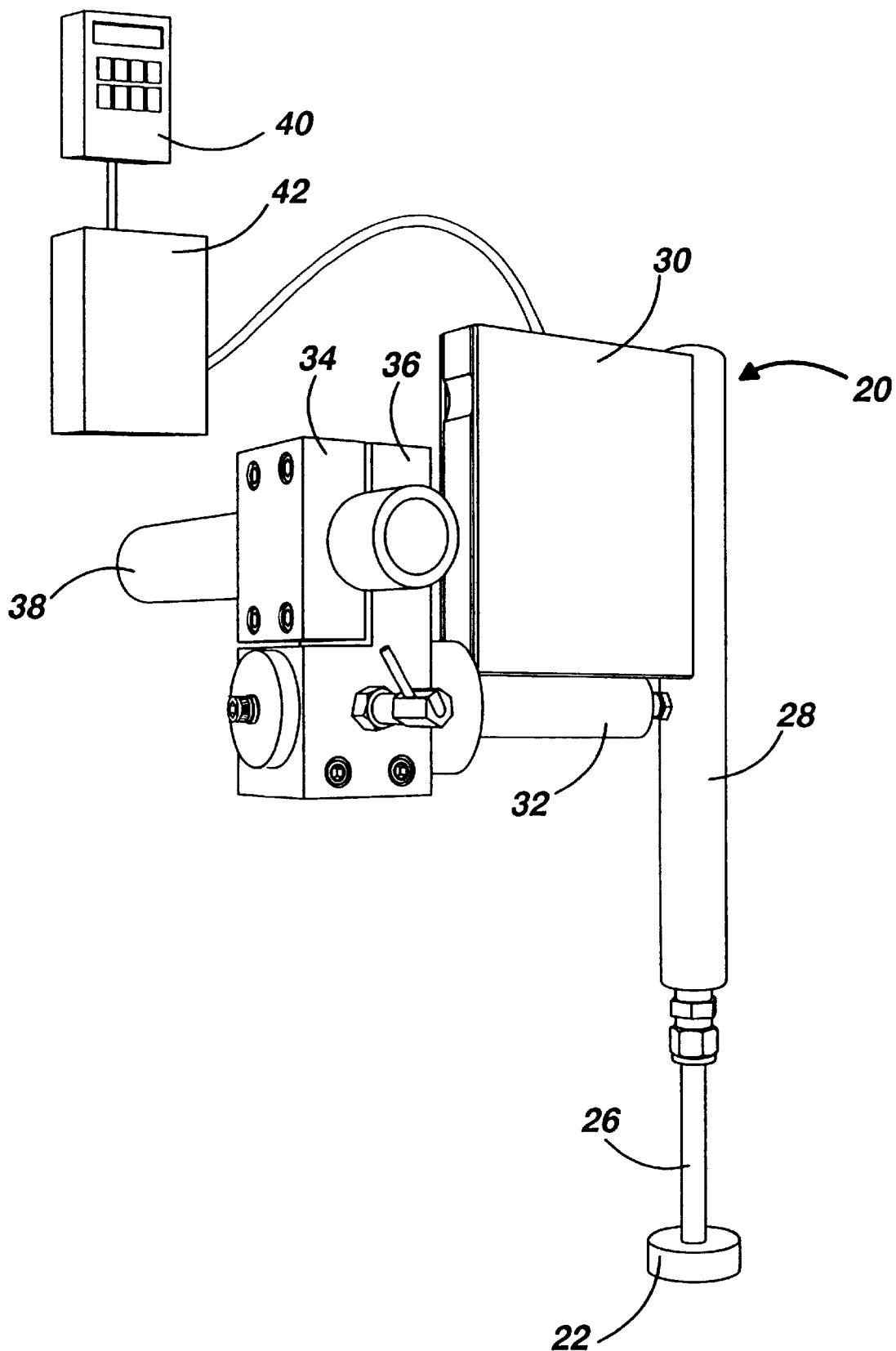
FIG. 2 is a perspective view of the moisture sensor according to the present invention.

Further features, objects and advantages will be evident from the following detailed description of the preferred embodiments of the present invention taken in conjunction with the accompanying drawings. FIGS. 1 and 2 illustrate a preferred embodiment of the present moisture sensor wherein there is shown a conveyor 10 comprising a series of wheels 12 supporting and moving belt 14. The movement of the belt is indicated by arrow 16. Particulate or granular material 18 such as ore concentrate is deposited on belt 14 and while moving, impinges on sensor 20 which comprises a disk 22 coupled to a rod preferably divided in a lower section 26 screwed to an upper section 28. Lower section 26 can therefore be easily replaced when necessary, for example, because of wear. Upper section 28 is screwed, welded, attached or otherwise secured to a force transducer 30, such as for example transducer model No.:462-D3-20 10PI manufactured and sold by Transducers Inc. from Cerritos, Calif. Transducer 30 is secured to a shelf 32 and the whole arrangement is secured on a wall, a ceiling or any other support means, such as, for example, brackets 34 and 36 surrounding a pipe 38, the pipe having each end secured on two posts (not shown) located on each side of the conveyor. When the conveyor is in operation, the force exerted by moving granular material on disk 22 is akin to the viscous drag. The force is transmitted to force transducer 30, and the signal generated by the transducer is processed by processing means 42 and displayed to the operator on a display 40. Preferably, processing means 42 allow the averaging of the signal before being displayed to reduce signal irregularities caused by lumps and other irregularities in the concentrate feed.

In practice, disk 22 could be eliminated or replaced with an element of basically any shape. However, it has been found that a disk-shape element is preferred for several reasons. Because the surface impinging on the particulate material is substantially round, it prevents the build-up of material on the surface thereof, which could significantly alter the accuracy of the measurements, and cause problems of other nature to the conveyor and/or the belt. Further, because the upper and lower surfaces of the disk are substantially flat, it also prevents axial forces, ie., perpendicular to the movement of particulate material, to be exerted on the probe. These forces are not only useless because they are not measured, but they may also cause damages to the sensor in the long run.

In a another embodiment of the invention, instead of having the force transducer externally coupled to the rod, the force transducer may itself be buried in the particulate material. Such embodiment is rendered possible with force transducers like strain gauges that are of relatively small size and can therefore be inserted, for example, within a casing or rod., which is subsequently buried within the bulk of the particulate material. However, it is obviously preferred to have the transducer outside of the particulate material to prevent any damages thereon.

Another major advantage of the present moisture sensor is that the measurements are taken within the bulk, therefore significantly reducing the risks of measurements being remote from the bulk moisture content.

Figure 3:
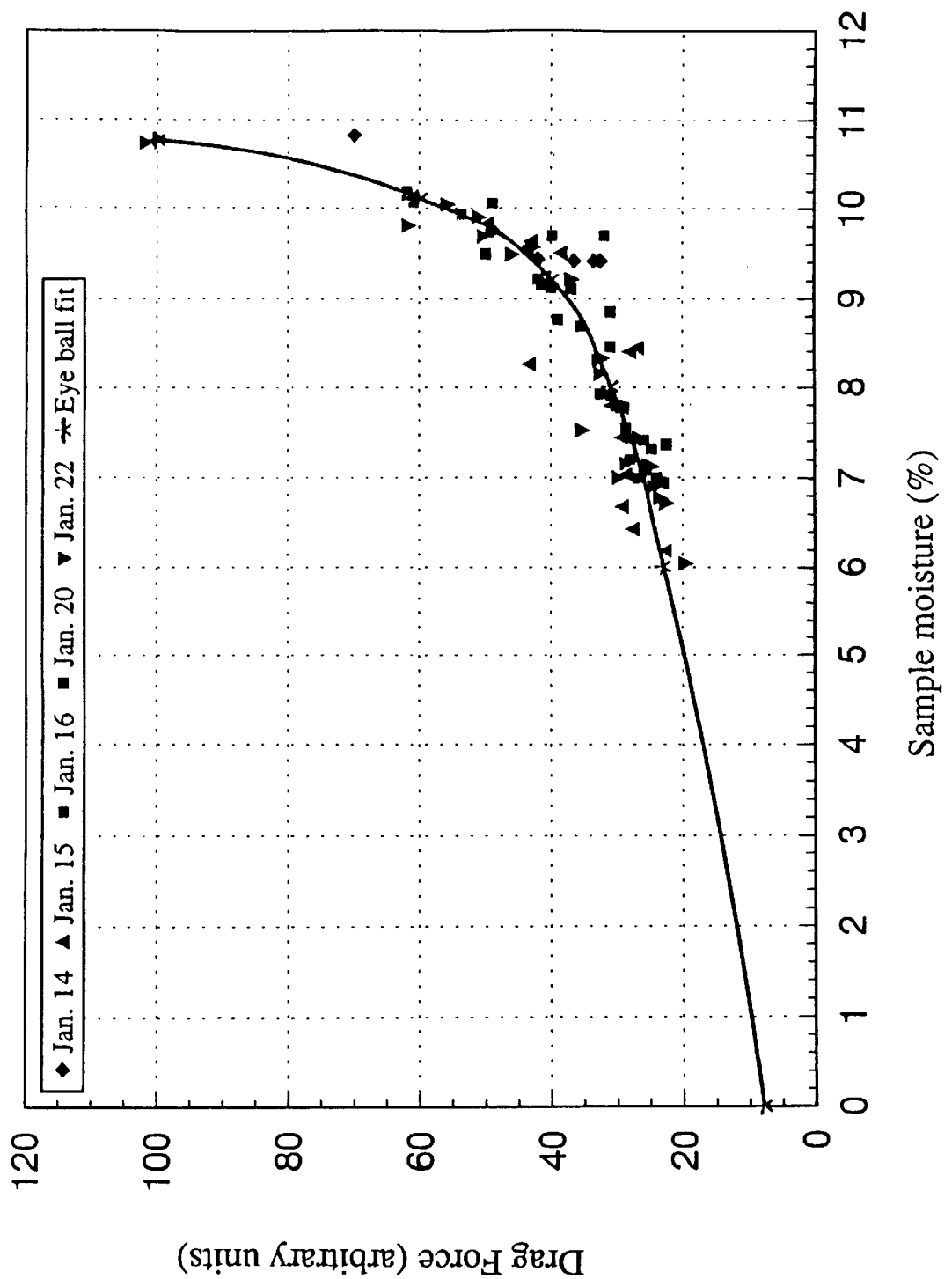
FIG. 3 illustrates an experimental diagram showing the drag force vs. the concentrate moisture.

As illustrated in FIG. 3, the moisture content of the concentrate is directly related to the drag force exerted on sensor 20. Following appropriate calibration, the operator can therefore easily determine, either by means of a calibration chart, or by the output of a calibration computer, the moisture content of the ore concentrate on the conveyor. The present moisture sensor is therefore completely independent from the electrical and optical properties of both the measured concentrate and the impurities in the associated water. The present sensor is also extremely easy to install, and can in fact be set on any conveying system.

The rod or casing is preferably made of a rigid material strong enough to resist the drag forces applied thereon, as well as other factors like rust or wear. Stainless steel has proven to be particularly advantageous.

It is not unusual that the height of particulate material or the uniformity of the surface thereof on the conveyor belt vary while the conveyor is in operation, thereby causing the disk-shaped element or part thereof to be outside of the bulk of the particulate material travelling on the belt. To minimize the risks of such occurrence, the lower surface of the disk-shaped element should be as close as possible to the belt. Alternately, appropriate baffles can be installed beforehand to ensure that a certain degree of uniformity and height is maintained when the particulate material passed through the sensor. Such baffles can be easily installed by any one of ordinary skill in the art.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains, and as may be applied to the essential features hereinbefore set forth, and as follows in the scope of the appended claims.

What is claimed is:

1. A moisture sensor for on-line monitoring the moisture content of moving particulate material, the sensor comprising a body coupled to a force transducer; processing means coupled to the force transducer to process signal output from the force transducer, and display means coupled to the processing means to display the moisture content of the particulate material, whereby the body is buried within the bulk of the moving particulate material and the signal output is generated from the force transducer as a result of the drag force exerted by the moving particulate material on the body.

2. A sensor according to claim 1 wherein the body is a rod having one end buried within the bulk of the particulate material and the other end coupled to the force transducer outside the particulate material.

3. A sensor according to claim 2 wherein the end of the rod buried within the bulk of the particulate material is provided with a disk-shape element.

4. A sensor according to claim 3 wherein the upper and lower surfaces of the disk-shape element are substantially perpendicular to the rod.

5. A sensor according to claim 1 wherein the particulate material is ore concentrates.

6. A sensor according to claim 1 wherein the processing means average the signal output and reduce signal output irregularities.

7. A moisture sensor for on-line monitoring the moisture content of conveyor borne particulate material, the sensor comprising a rod having one end provided with a disk-shaped element to be buried within the bulk of the particulate material, and the other end coupled to a force transducer; processing means coupled to the force transducer to process signal output from the force transducer, and display means coupled to the processing means to display the moisture content of the particulate material, whereby the signal output is generated from the force transducer as a result of the drag force exerted by the moving particulate material on the body.

8. A sensor according to claim 7 wherein the upper and lower surfaces of the disk-shape element are perpendicular to the rod.

9. A sensor according to claim 7 wherein second processing means average the signal output and reduce signal output irregularities.

* * * * *